(12) United States Patent
Wiesman et al.

(10) Patent No.: US 12,290,578 B2
(45) Date of Patent: *May 6, 2025

(54) COUPLING AGENT PRODUCED FROM NATURALLY FERMENTED AND SUSTAINABLE ADDITIVES

(71) Applicant: Wiesman Holdings, LLC, York, PA (US)

(72) Inventors: Jon Wiesman, York, PA (US); George Deckner, Cincinnati, OH (US)

(73) Assignee: Wiesman Holdings, LLC, York, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/450,873

(22) Filed: Aug. 16, 2023

(65) Prior Publication Data

US 2023/0390420 A1     Dec. 7, 2023

Related U.S. Application Data

(63) Continuation of application No. 17/561,171, filed on Dec. 23, 2021, now Pat. No. 11,786,614, which is a
(Continued)

(51) Int. Cl.
| | |
|---|---|
| *A61K 49/22* | (2006.01) |
| *A61K 31/045* | (2006.01) |
| *A61K 47/02* | (2006.01) |
| *A61K 47/10* | (2017.01) |
| *A61K 47/18* | (2017.01) |
| *A61K 47/24* | (2006.01) |

(Continued)

(52) U.S. Cl.
CPC .......... *A61K 49/226* (2013.01); *A61K 31/045* (2013.01); *A61K 47/02* (2013.01); *A61K 47/10* (2013.01); *A61K 47/183* (2013.01); *A61K 47/24* (2013.01); *A61K 47/32* (2013.01); *A61K 47/36* (2013.01)

(58) Field of Classification Search
CPC ..................................... A61K 49/226
See application file for complete search history.

(56) References Cited

U.S. PATENT DOCUMENTS

| | | | |
|---|---|---|---|
| 3,304,262 A | 2/1967 | Corey | |
| 3,621,709 A | 11/1971 | Frey | |
| | (Continued) | | |

FOREIGN PATENT DOCUMENTS

| | | |
|---|---|---|
| WO | 2005004972 A1 | 1/2005 |
| WO | 2005004982 A2 | 1/2005 |
| WO | 2012009794 A1 | 1/2012 |

OTHER PUBLICATIONS

PCT International Search Report and Written Opinion, Application No. PCT/US2017/057344, Dated: Mar. 16, 2018, 10 pages.
(Continued)

*Primary Examiner* — Benjamin J Packard
(74) *Attorney, Agent, or Firm* — Barley Snyder

(57) ABSTRACT

A coupling agent composition is provided and includes a plurality of non-toxic components in an amount equal to or greater than 97 weight percent (wt %). The coupling agent composition includes a carrier of water, at least one water soluble polyol selected from the group consisting of propanediol, pentylene glycol, and butylene glycol in an amount of from about 1.0 to about 20.0 wt %, a thickening agent in an amount of about 0.05 to about 5.00 wt %, and a balance of incidental impurities.

15 Claims, 1 Drawing Sheet

Related U.S. Application Data continuation of application No. 16/848,502, filed on Apr. 14, 2020, now Pat. No. 11,241,508, which is a continuation of application No. 15/297,762, filed on Oct. 19, 2016, now Pat. No. 10,646,597.

(51) Int. Cl.
*A61K 47/32* (2006.01)
*A61K 47/36* (2006.01)

(56) References Cited

U.S. PATENT DOCUMENTS

| | | | |
|---|---|---|---|
| 3,740,421 | A | 6/1973 | Schmolka et al. |
| 3,826,127 | A | 7/1974 | Molina |
| 4,002,221 | A | 1/1977 | Buchalter |
| 4,365,516 | A | 12/1982 | Molina |
| 5,246,490 | A | 9/1993 | Kehoe et al. |
| 5,522,878 | A | 6/1996 | Montecalvo |
| 6,302,848 | B1 | 10/2001 | Larson et al. |
| 8,133,516 | B2 | 3/2012 | Lauer |
| 8,618,175 | B2 | 12/2013 | Heinar |
| 2005/0215908 | A1 | 9/2005 | Chew et al. |
| 2006/0246111 | A1 | 11/2006 | Smith |
| 2009/0155325 | A1 | 6/2009 | Wenzel et al. |
| 2010/0215700 | A1 | 8/2010 | Moaddel et al. |
| 2011/0229446 | A1 | 9/2011 | Roman et al. |
| 2012/0114584 | A1 | 5/2012 | Woghiren et al. |
| 2012/0150033 | A1 | 6/2012 | Rauch |

OTHER PUBLICATIONS

Enhancement of (R)-1,3-Butanediol Production by Engineered *Escherichia coli* Using a Bioreactor System With Strict Regulation of Overall Oxygen Transfer Coefficient and Ph; Naoya Kataoka et al. Bioscience, Biotechnology and Biochemistry, vol. 78, Issue 4, Apr. 23, 2014; http://dx.doi.org/10.1080/09168451.2014.891933). • http://dx.doi.org/10.1080/09168451.2014.891933, 6 pages.

California Proposition 65 (1986) (see http://oehha.ca.gov/proposition-65/proposition-65-list).

Doelker, E., "Water Swollen Cellulose Derivatives in Pharmacy", Hydrogels in Medicine and Pharmacy: vol. 2—Polymers, edited by Peppas, N.A., CRC Press Inc., Boca Raton, Florida, 1987, p. 124.

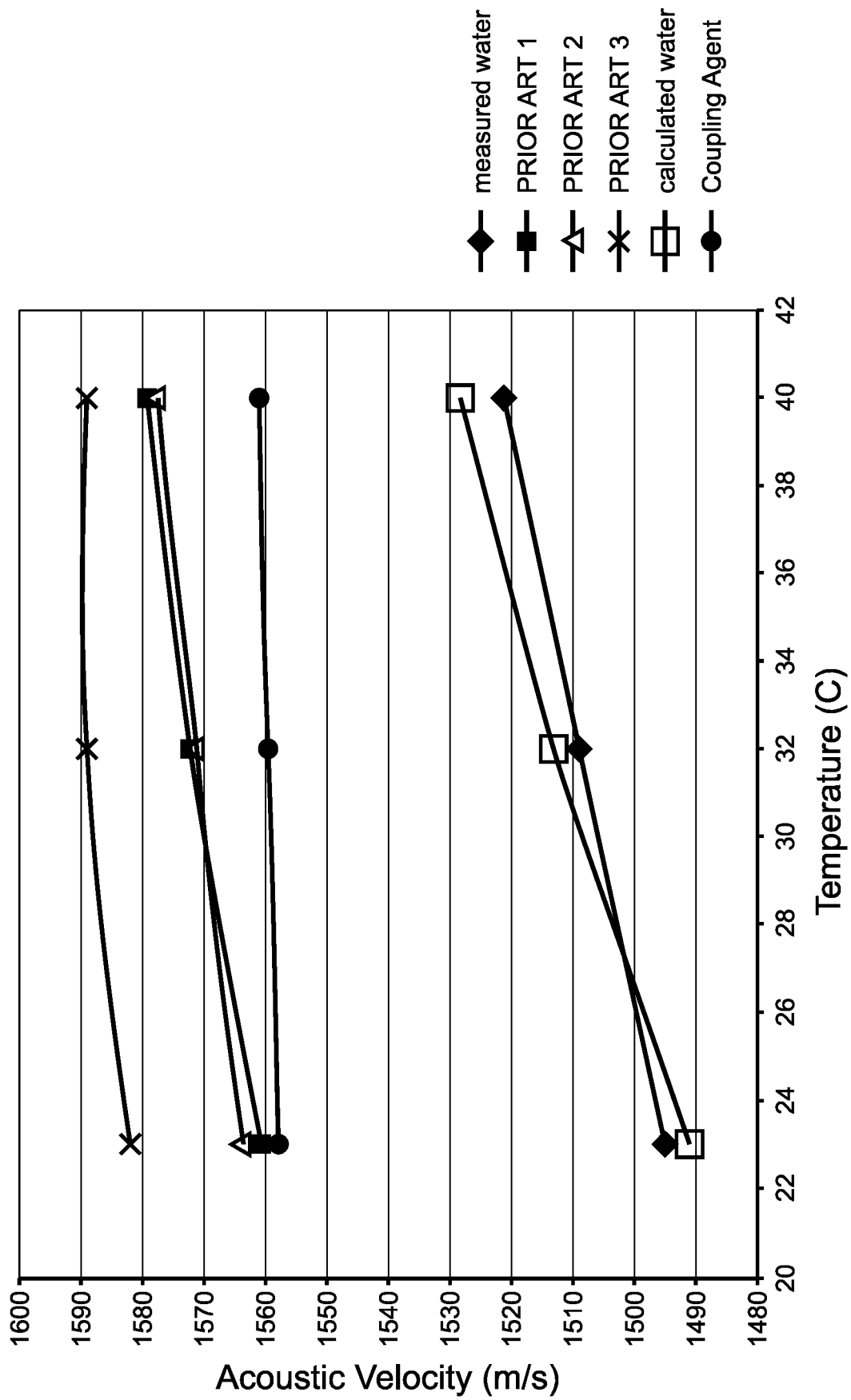

COUPLING AGENT PRODUCED FROM NATURALLY FERMENTED AND SUSTAINABLE ADDITIVES

CROSS-REFERENCE TO RELATED APPLICATIONS

This application is a continuation of U.S. patent application Ser. No. 17/561,171, filed Dec. 23, 2021, U.S. patent application Ser. No. 15/297,762, filed Oct. 19, 2016, and issued as U.S. Pat. No. 10,646,597, and U.S. patent application Ser. No. 16/484,502, filed Apr. 14, 2020, claiming priority under 35 U.S.C. § 119.

FIELD OF THE INVENTION

The invention relates to a coupling agent and, more particularly, a coupling agent containing naturally fermented and sustainable additives.

BACKGROUND

An ultrasound coupling agent, otherwise known as a "gel", is designed to act as a conductive barrier between an ultrasound probe and the outer layer of skin, known as the epidermis. A gel providing excellent acoustics is a necessity in order to produce the appropriate reflection of sound waves useful to a valid diagnosis.

In order to properly transmit ultrasonic impulses, the gel must be a medium that can uniformly produce uninterrupted quantitative parameters for measurement of acoustic velocity, impedance, and attenuation. These parameters are all necessary to yield a competent diagnosis via ultrasound technology.

Ultrasound diagnostic procedures are used in assessing and diagnosing a wide variety of medical conditions related to internal organs. Perhaps the condition most familiar to the general public is with regard to development of a fetus during pregnancy. Ultrasonography uses ultrasound scanning to produce images on a cathode ray tube or television screen. It is widely used in obstetrics for several purposes, including confirming pregnancy under circumstances where hormonal tests cannot be used, for establishing gestational age and the number of fetuses, for determining sex of the fetus, for detecting fetal abnormalities or fetal death, for monitoring fetal growth, as an adjunct to amniocentesis, etc. Ultrasound Doppler scanning may also be used to test fetal blood flow. Ultrasonography is a valuable technique, since it provides a safe alternative to roentographic or X-ray techniques.

The procedure typically will involve the application of a gel to the patient's abdomen. A piezoelectric transducer that generates sound waves at a frequency in the range of 2.25 to 7.0 MHz is placed in the gel and moved across the abdomen to form images at different angles. The sound waves reflect off tissues to produce an echo signal that can be converted to images that can be viewed on a screen and interpreted by a competent medical practitioner. The gel lubricates the abdomen and prevents the sound waves from being trapped or reflected by air pockets that might distort the image and lead to an incorrect diagnosis. Typically, after completion of the ultrasound examination, any remaining gel is wiped off the patient's abdomen. For instance, U.S. Pat. No. 8,133,516 discloses lubricants used for medicinal purposes and to skin care compositions, and particularly to a therapeutic ultrasound gel used as a lubricant during ultrasonography procedures that enhances the transmission of sound waves and that also helps to prevent the formation of stretch marks.

While several gels are available, there is still a need for a gel that can enhance the transmission of sound waves from the transducer into the abdominal cavity while at the same time containing ingredients that are medically safe and non-toxic.

Coupling agents have never fit into the "environmentally friendly and sustainable" category because of the chemical formulation(s) typically used in manufacturing. The known commercially available coupling agents have high concentrations of known irritants like propylene glycol or suspected estrogen mimics such as parabens. These molecules are synthetically derived from other than renewable materials.

Increasingly, manufacturers of personal care products are responding to customer interest in more environmentally friendly and sustainably sourced products. Regulatory schemes including those of federal and state governments increasingly reflect these concerns, as well.

Propylene glycol is a known general purpose coupling agent that is often used in ambient temperature in thickness gauging applications on smooth surfaces. Glycerin is also another known general purpose coupling agent, but it is more viscous and has higher acoustic impedance than propylene glycol. This property makes it a preferred coupling agent for rough surfaces and highly attenuating materials. However, these and other known ultrasound coupling agents typically have high concentrations of known irritants and/or estrogen mimics. In fact, many of these known coupling agents include one or more toxic components known to be toxic under California Proposition 65 (1986) (see http://oehha.ca.gov/proposition-65/proposition-65-list).

The United States Department of Agriculture (USDA) set forth organic regulations in the Federal Code of Regulations (CFR) in Title 7, subtitle 205. Accordingly, a nontoxic component is a component not known to cause any adverse physiological effects in animals, plants, humans, or the environment. Under § 205.200—General—the producer or handler of a production or handling operation intending to sell, label, or represent agricultural products as "100 percent organic," "organic," or "made with organic (specified ingredients or food group(s))" must comply with the applicable provisions of this subpart. As a result, production practices implemented in accordance with that section must maintain or improve the natural resources of the operation, including soil and water quality.

Thus, it is desirable to obtain a coupling agent having one or more non-toxic components that are environmentally friendly and sustainable and derived from a natural resource that utilizes the resource, it constituent parts, and its by-products in a variety of uses and in a manner that reduces waste.

SUMMARY

A coupling composition is provided and includes a plurality of non-toxic components in an amount equal to or greater than 97 weight percent (wt %). The coupling agent composition includes a carrier of water, at least one water soluble polyol selected from the group consisting of propanediol, pentylene glycol, and butylene glycol in an amount of from about 1.0 to about 20.0 wt %, a thickening agent in an amount of about 0.05 to about 5.00 wt %, and a balance of incidental impurities.

BRIEF DESCRIPTION OF THE DRAWINGS

FIG. 1 is a comparative chart displaying measured acoustic velocities for various known coupling agents and a proposed coupling agent according to the invention.

DETAILED DESCRIPTION OF THE EMBODIMENT(S)

The following text sets forth a broad description of various exemplary embodiments of the invention. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents, and other references mentioned herein are incorporated by reference in their entireties for all purposes.

Unless otherwise specified, when the following abbreviations are used herein, they have the following meaning:

As used herein, the terms "comprises," "comprising," "includes," "including," "has," "having," "contains," or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, that is, occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, alternatively within 5% of the reported numerical value.

"Biomass" as used herein refers to a natural product containing hydrolyzable polysaccharides that provide fermentable sugars including any sugars and starch derived from natural resources such as corn, sugar cane, wheat, cellulosic or lignocellulosic material and materials comprising cellulose, hemicellulose, lignin, starch, oligosaccharides, disaccharides and/or monosaccharides, and mixtures thereof. Biomass may also comprise additional components such as protein and/or lipids. Biomass may be derived from a single source or biomass can comprise a mixture derived from more than one source. For example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, waste sugars, wood and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, trees, branches, roots, leaves, wood chips, sawdust, shrubs and bushes, vegetables, fruits, flowers, animal manure, and mixtures thereof. For example, mash, juice, molasses, or hydrolysate may be formed from biomass by any processing known in the art for processing the biomass for purposes of fermentation such as by milling, treating, and/or liquefying and comprises fermentable sugar and may comprise water. For example, cellulosic and/or lignocellulosic biomass may be processed to obtain a hydrolysate containing fermentable sugars by any method known to one skilled in the art.

An aqueous feed stream may be derived or formed from biomass by any processing known in the art for processing the biomass for purposes of fermentation such as by milling, treating, and/or liquefying and comprises fermentable carbon substrate (e.g., sugar) and may comprise water.

"Feedstock" as used herein means a feed in a fermentation process, the feed containing a fermentable carbon source with or without undissolved solids, and where applicable, the feed containing the fermentable carbon source before or after the fermentable carbon source has been liberated from starch or obtained from the breakdown of complex sugars by further processing such as by liquefaction, saccharification, or other process. Feedstock includes or is derived from a biomass. Suitable feedstocks include, but are not limited to, rye, wheat, corn, corn mash, sugarcane, cane mash, barley, cellulosic material, lignocellulosic material, or mixtures thereof. Where reference is made to "feedstock oil," it will be appreciated that the term encompasses the oil produced from a given feedstock.

"Fermentation medium" as used herein means the mixture of water, sugars, dissolved solids, optionally microorganisms producing alcohol, product alcohol, and all other constituents of the material held in the fermentation vessel in which product alcohol is being made by the reaction of sugars to alcohol, water, and carbon dioxide ($CO_2$) by the microorganisms present. At the end of a fermentation run the sugars may be depleted from the fermentation medium. From time to time, as used herein the term "fermentation broth" and "fermented mixture" can be used synonymously with "fermentation medium."

"Fermentable carbon source" or "fermentable carbon substrate" as used herein means a carbon source capable of being metabolized by the microorganisms disclosed herein for the production of fermentative alcohol. Suitable fermentable carbon sources include, but are not limited to, monosaccharides such as glucose or fructose; disaccharides such as lactose or sucrose; oligosaccharides; polysaccharides such as starch or cellulose; C5 sugars such as xylose and arabinose; one carbon substrates including methane; and mixtures thereof.

"Fermentable sugar" as used herein refers to one or more sugars capable of being metabolized by the microorganisms disclosed herein for the production of fermentative alcohol.

"Sugar" as used herein refers to oligosaccharides, disaccharides, monosaccharides, and/or mixtures thereof. The term "saccharide" also includes carbohydrates including starches, dextrans, glycogens, cellulose, pentosans, as well as sugars.

As used herein, "recombinant microorganism" refers to microorganisms such as bacteria or yeast, that are modified by use of recombinant DNA techniques, for example, by engineering a host cell to comprise a biosynthetic pathway such as a biosynthetic pathway to produce an a polyol such as propanediol.

"Renewable resource" refers to a natural resource that can be replenished within a 100 year time frame. The resource may be replenished naturally, or via agricultural techniques. Renewable resources include plants, animals, fish, bacteria, fungi, and forestry products. They, may be naturally occurring, hybrids, or genetically engineered organisms. Natural resources such as crude oil, coal, and peat which take longer than 100 years to form are not considered to be renewable resources.

"Organic natural resource materials" are resources that can be replenished, either through biological reproduction or other naturally reoccurring processes in a finite amount of time. Organic natural resources are known to be environmentally friendly and sustainable.

Throughout the specification a "natural" material is one which has been harvested, mined or collected, and which subsequently may have been processed, without chemical reaction, to yield a chemical or chemicals that are identifiable in the original source material. The phrase "without chemical reaction" permits washing, decolorizing, distilling, grinding, milling, separating and/or concentrating the material by physical means. By "naturally derived", we mean materials wherein the majority of the molecule (by weight) is derived from natural materials.

According to the present invention, it has been found that the above objects and advantages can be accomplished through an ultrasound coupling agent having a composition with one or more non-toxic components greater than 97 weight percent (wt %).

In an embodiment of the invention, the coupling agent composition includes a plurality of non-toxic components derived from one or more organic natural resource material and in an amount equal to or greater than 97 wt %, a thickening agent in an amount of 0.05-5 wt %, and a balance of incidental impurities.

In an exemplary embodiment of the invention, the one or more non-toxic components includes a carrier and an organic natural resource material.

In a proposed coupling agent composition, the carrier is water, preferably deionized water or distilled water. In particular, the parts of water are 75.00-98.00 wt % in the proposed coupling agent composition. In another exemplary embodiment of the invention, the proposed coupling agent composition includes a carrier having a wt % range of 85.00-90.00%. In another exemplary embodiment of the invention, the proposed coupling agent composition includes a carrier having a wt % range of 87.00-89.00%.

One skilled in the art should appreciate that the carrier can be various known water types, including water that has been neutralized with an alkali hydroxide such as sodium hydroxide or potassium hydroxide to a pH value in the range of 6.0 to 8.0.

According to the invention, the organic natural resource material is extracted and/or produced from one or more organic natural resources using known fermentation and/or enzymatic synthesis. For instance, the fermentation and/or enzymatic synthesis may be a known natural chemical process in which bacteria or yeast converts organic materials, such as sugars or biomass waste streams, into various types of high value-added chemicals.

According to the invention, the organic natural resource material is at least one water soluble polyol. In particular, the parts of soluble polyol are 1.00-25.00 wt % in the proposed coupling agent composition. In another exemplary embodiment of the invention, the proposed coupling agent composition includes a soluble polyol having a wt % range of 5.00-15.00%. In another exemplary embodiment of the invention, the proposed coupling agent composition includes a soluble polyol having a wt % range of 9.00-11.00%.

The at least one water soluble polyol is selected from the group consisting of propanediol, pentylene glycol, and butylene glycol.

Naturally fermented glycols such as propanediol, butylene glycol, and pentylene glycol are useful in the proposed coupling agent composition. Pentylene glycol is a humectant used in cosmetics and beauty products that is also secondarily used as a solvent and preservative potentiator. It is both water- and oil-soluble and can have moisture-binding and antimicrobial properties that are well known to one skilled in the art.

In an exemplary embodiment, the at least one water soluble polyol is propanediol, and more specifically is 1,3-propanediol. The propanediol is a colorless and highly pure glycol derived from a known sustainable and renewable corn sugar fermentation process. This is a 100 percent bio-based ingredient that boosts preservative efficacy and eliminates skin irritation caused by glycols used in known coupling agents. For instance, known 1,3-propanediol, such as the brand Zemea® (DuPont Tate & Lyle Bio Products), can be used to replace non-biologically derived glycols used in known coupling agents, such as propylene glycol (1,2-propanediol), butylene glycol (1,3-/1/4-butanediol), and glycerin.

In another exemplary embodiment, the pentylene glycol is 1,5-pentanediol and may be used as the at least one water soluble polyol. The 1,5-pentanediol is used as an alternative to known glycols and may be derived through known processes such as hydrogenation of glutaric acid and its derivatives or hydrogenation of furfural followed by hydrogenolysis of the substituted tetrahydrofuran. For instance, known pentylene glycol, such as the brand Diol PD™ (Kokyu Alcohol Kogyo Co. Ltd.) can be used to replace synthetically derived glycols used in known coupling agents, such as propylene glycol (1,2-propanediol) or glycerin.

In another exemplary embodiment, the at least one water soluble polyol is butylene glycol, and more specifically is 1,3-butanediol. The butylene glycol is used as an alternative to known glycols and may be derived from biomass-derived glucose using known processes. In one known process, genetically- and metabolically-engineered *Escherichia coli* are cultured in fed-batch fermentation. The 1,3-butylene glycol metabolic pathway consists of four enzymatic steps from acetyl-CoA and uses phaA encoding acetyl-CoA acetyltranferase from *Ralstonia eutropha*; phaB encoding NADPH-dependent acetacetyl-CoA reductase from *R. eutropha*; bld encoding butyryl-CoA dehydrogenase from *Clostridium saccharoperbutylacetonicum*; and adh encoding alcohol dehydrogenase inherent in the host strain *E. coli* BW lacI$^q$. (Enhancement Of (R)-1,3-Butanediol Production By Engineered *Escherichia Coli* Using A Bioreactor System With Strict Regulation Of Overall Oxygen Transfer Coefficient and Ph; Naoya Kataoka et al. Bioscience, Biotechnology and Biochemistry, Vol. 78, Issue 4, 2014-04-23; http://dx.doi.org/10.1080/09168451.2014.891933). For instance, known 1,3-butylene glycol, such as the brand Haisugarcane BG (CAS RN 107-88-0) (Kokyu Alcohol Kogyo Co. Ltd.) can be used to replace glycols used in known coupling agents, such as propylene glycol (1,2-propanediol) or glycerin.

According to the invention, a fermentation and/or enzymatic synthesis uses bacteria or yeast to convert organic materials, such as sugars or biomass waste, into the water soluble polyol. The water soluble polyol is then combined with the carrier to provide a proposed coupling agent composition.

In the proposed coupling agent composition, the thickening agent is a rheology modifier with parts of the composition of 0.00-5.00 wt %. In another exemplary embodiment of the invention, the proposed coupling agent composition includes a thickening agent having a wt % range of 0.10-1.00%. In another exemplary embodiment of the invention, the proposed coupling agent composition includes a thickening agent having a wt % range of 0.05-0.70%.

In an exemplary embodiment, the thickening agent is a non-toxic soluble or swellable polymer. In particular, the thickening agent may be a cross-linked polymer selected from a group consisting of hydrophobic polyacrylate or hydrophilic polyacrylate. The thickening agent may be natural or synthetic. If the thickening agent is synthetic, then the thickening agent portion of the proposed coolant gel composition is less than or equal to 3.00 wt %, according to an exemplary embodiment of the invention.

According to the invention, the thickening agent may include a crosslinked polyacrylate, which may be selected from a group consisting of carbomer, sodium acryloyldimethyltaurate/VP Crosspolymer, acrylates/C10-30 alkyl acrylate crosspolymer, or crosslinked PVP. In another exemplary embodiment of the invention, the proposed coupling agent composition includes a crosslinked polyacrylate having a wt % range of 0.10-2.00%.

In an exemplary embodiment, the crosslinked polyacrylate is carbomer, which is used to achieve desired rheological properties in the proposed coupling agent composition. For instance, known carbomer, such as the brand Carbopol® Ultrez 30 Polymer (The Lubrizol Corporation, Wickliffe, OH) can be used.

In an exemplary embodiment, the crosslinked polyacrylate is a sodium acryloyldimethyltaurate/VP crosspolymer. The sodium acryloyldimethyltaurate/VP crosspolymer may be used to achieve desired rheological properties in the proposed coupling agent composition. For instance, known sodium acryloyldimethyltaurate/VP crosspolymer, such as the brand Aristoflex® (AVS) (Clariant Corporation, Charlotte, NC) can be used.

In another exemplary embodiment, the crosslinked polyacrylate is an acrylate/C10-30 alkyl acrylate crosspolymer, which may be used to achieve desired rheological properties in the proposed coupling agent composition. For instance, a known acrylate/C10-30 alkyl acrylate crosspolymer, such as the brand Carbopol® Ultrez 21 (The Lubrizol Corporation, Wickliffe, OH), can be used.

In another exemplary embodiment, the crosslinked polyacrylate is crosslinked polyvinylpyrrolidone (PVP). The crosslinked PVP is used to achieve desired rheological properties in the proposed coupling agent composition. For instance, a known crosslinked PVP, such as the brand FlexiThix™ (Ashland Inc., Covington, KY), can be used.

According to the invention, the thickening agent may include one or more naturally derived additives. In another exemplary embodiment of the invention, the proposed coupling agent composition includes one or more naturally derived additives having a wt % range of 0.50-3.00%. In an exemplary embodiment of the invention, the one or more naturally derived additives is a soluble polymer and may be selected from a group consisting of xanthan gum, guar, locust bean, sodium hyaluronate, glucomannan, carrageenan, sodium alginate, acacia, tara gum, tamarind seed, mannan, succinoglycan, microcrystalline cellulose, and scleroglucan.

In an exemplary embodiment of the invention, the proposed coupling agent composition includes a thickening agent additive having a wt % range of 0.10-3.00%. In another exemplary embodiment of the invention, the proposed coupling agent composition includes a thickening agent additive having a wt % range of 0.2-2.00%. In another exemplary embodiment of the invention, the proposed coupling agent composition includes a thickening agent additive having a wt % range of 0.10-0.30%. In yet another exemplary embodiment of the invention, the proposed coupling agent composition includes a thickening agent additive having a wt % range of 1.60-1.80%.

According to the invention, the proposed coupling agent composition may include a biocide agent. The biocide agent may be in a range of 0.25 to 1 weight percent of the proposed coupling agent composition. The biocide agent may be selected from a group consisting of phenoxyethanol, benzyl alcohol, caprylyl glycol, ethylhexylglycerin, decylene glycol, glyceryl caprylate, and 1,2-hexanediol.

In an exemplary embodiment of the invention, the proposed coupling agent composition includes a biocide agent having a wt % range of 0.10-1.00%. In another exemplary embodiment of the invention, the proposed coupling agent composition includes a biocide agent having a wt % range of 0.25-0.60%. In another exemplary embodiment of the invention, the proposed coupling agent composition includes a biocide agent having a wt % of 0.50%.

According to the invention, the proposed coupling agent composition may also include a neutralizing agent. The neutralizing agent may be in a range of 0.05 to 0.50 weight percent of the proposed coupling agent composition. The neutralizing agent may be selected from a group consisting of sodium hydroxide, triethanolamine, tromethamine, arginine, and lysine.

In an exemplary embodiment of the invention, the proposed coupling agent composition includes a neutralizing agent having a wt % range of 0.00-1.00%. In another exemplary embodiment of the invention, the proposed coupling agent composition includes a neutralizing agent having a wt % range of 0.10-0.30%. In another exemplary embodiment of the invention, the proposed coupling agent composition includes a neutralizing agent having a wt % range of 0.20-0.25%.

According to the invention, the proposed coupling agent composition may also include a chelating agent. The chelating agent may be in a range of 0.025 to 0.10 weight percent of the proposed coupling agent composition. The neutralizing agent may be selected from a group consisting of disodium EDTA and sodium phytate.

In an exemplary embodiment of the invention, the proposed coupling agent composition includes a chelating agent having a wt % range of 0.01-1.00%. In another exemplary embodiment of the invention, the proposed coupling agent composition includes a chelating agent having a wt % range of 0.03-0.07%. In another exemplary embodiment of the invention, the proposed coupling agent composition includes a neutralizing agent having a wt % of 0.05%.

According to the invention, the proposed coupling agent composition may include filler materials or have a balance of incidental impurities.

The present invention can be illustrated by the following examples of proposed coupling agent compositions according to the invention without being limited by them. Each of the following examples was prepared being dependent on an organic natural resource material in view of overall percentage of non-toxic component.

Table 1 shows an exemplary embodiment of a proposed coupling agent composition according to the invention.

TABLE 1

| Compositional Element | Weight Percent (wt %) |
|---|---|
| Carrier | 75.00-98.00% |
| Organic natural resource material | 1.00-25.00% |
| Thickening agent | 0.10-1.00% |
| Biocide agent | 0.10-1.00% |
| Neutralizing agent | 0.10-0.30% |
| Thickening agent additive | 0.10-1.00% |
| Chelating agent | 0.05% |
| Percent Natural | ~97.00-100% |

Table 2 shows another exemplary embodiment of a proposed coupling agent composition according to the invention.

TABLE 2

| Compositional Element | Weight Percent (wt %) |
|---|---|
| Carrier | 75.00-98.00% |
| Organic natural resource material | 1.00-25.00% |
| Thickening agent additive | 0.10-0.30% |
| Biocide agent | 0.10-1.00% |
| Chelating agent | 0.01-0.05% |
| Percent Natural | ~97.00-100% |

Table 3 shows an exemplary embodiment of a proposed coupling agent composition according to the invention.

TABLE 3

| Compositional Element | Weight Percent (wt %) | Weight Percent (wt %) |
|---|---|---|
| Deionized water | 75.00-98.00% | 88.43% |
| Propanediol | 1.00-25.00% | 10.00% |
| Acrylate/C10-30 alkyl acrylate crosspolymer | 0.10-1.00% | 0.60% |
| Benzyl alcohol | 0.10-1.00% | 0.50% |
| Sodium Hydroxide | 0.10-0.30% | 0.22% |
| Xanthan gum | 0.10-1.00% | 0.20% |
| Disodium EDTA | 0.05% | 0.05% |
| Percent Natural | ~97.00-100% | 98.63% |

Table 4 shows another exemplary embodiment of a proposed coupling agent composition according to the invention.

TABLE 4

| Compositional Element | Weight Percent (wt %) | Weight Percent (wt %) |
|---|---|---|
| Deionized water | 75.00-98.00% | 88.43% |
| Propanediol | 1.00-25.00% | 10.00% |
| Acrylate/C10-30 alkyl acrylate crosspolymer | 0.10-1.00% | 0.60% |
| Benzyl alcohol | 0.10-1.00% | 0.50% |
| Sodium Hydroxide | 0.10-0.30% | 0.22% |
| Xanthan gum | 0.10-1.00% | 0.20% |
| Disodium EDTA | 0.05% | 0.05% |
| Percent Natural | ~97.00-100% | 98.63% |

Table 5 shows another exemplary embodiment of a proposed coupling agent composition according to the invention.

TABLE 5

| Compositional Element | Weight Percent (wt %) | Weight Percent (wt %) |
|---|---|---|
| Deionized water | 75.00-98.00% | 88.43% |
| 1,5-pentanediol | 1.00-25.00% | 10.00% |
| Acrylate/C10-30 alkyl acrylate crosspolymer | 0.10-1.00% | 0.60% |
| Benzyl alcohol | 0.10-1.00% | 0.50% |
| Sodium Hydroxide | 0.10-0.30% | 0.22% |
| Xanthan gum | 0.10-1.00% | 0.20% |
| Disodium EDTA | 0.05% | 0.05% |
| Percent Natural | ~97.00-100% | 98.63% |

Table 6 shows another exemplary embodiment of a proposed coupling agent composition according to the invention.

TABLE 6

| Compositional Element | Weight Percent (wt %) | Weight Percent (wt %) |
|---|---|---|
| Deionized water | 75.00-98.00% | 88.43% |
| 1,3-butanediol | 1.00-25.00% | 10.00% |
| Acrylate/C10-30 alkyl acrylate crosspolymer | 0.10-1.00% | 0.60% |
| Benzyl alcohol | 0.10-1.00% | 0.50% |
| Sodium Hydroxide | 0.10-0.30% | 0.22% |
| Disodium EDTA | 0.10-1.00% | 0.05% |
| Xanthan gum | 0.05% | 0.02% |
| Percent Natural | ~97.00-100% | 98.63% |

Table 7 shows another exemplary embodiment of a proposed coupling agent composition according to the invention.

TABLE 7

| Compositional Element | Weight Percent (wt %) | Weight Percent (wt %) |
|---|---|---|
| Deionized water | 75.00-98.00% | 87.75% |
| Pentylene Glycol | 1.00-25.00% | 10.00% |
| Carrageenan | 1.0-2.0% | 1.70% |
| Benzyl alcohol (natural sourced) | 0.10-1.00% | 0.50% |
| Xanthan Gum | 0.10-0.40% | 0.30% |
| Percent Natural | ~97.00-100% | 100.00% |

Table 8 shows an exemplary embodiment of a proposed coupling agent composition according to the invention.

TABLE 8

| Compositional Element | Weight Percent (wt %) | Weight Percent (wt %) |
|---|---|---|
| Deionized water | 75.00-98.00% | 87.55% |
| Carrageenan | 1.00-3.00% | 1.70% |
| Sodium Phytate | 0.05-0.20% | 0.05% |
| 1,3-Propanediol | 1.00-20.00% | 10.00% |
| Benzyl alcohol (natural sourced) | 0.10-1.50% | 0.50% |
| Xanthan Gum | 0.05-1.00% | 0.20% |
| Percent Natural | ~100% | ~100.00% |

Table 9 shows an exemplary embodiment of a proposed coupling agent composition according to the invention.

TABLE 9

| Compositional Element | Weight Percent (wt %) | Weight Percent (wt %) |
|---|---|---|
| Deionized water | 75.00-98.00% | 88.00 |
| Carrageenan | 1.00-3.00% | 1.70% |
| Sodium Phytate | 0.05-0.20% | 0.05% |
| Butylene Glycol | 1.00-20.00% | 10.00% |
| Benzyl alcohol (natural sourced) | 0.10-1.50% | 0.50% |
| Xanthan Gum | 0.05-1.00% | 0.20% |
| Percent Natural | ~100% | ~100.00% |

Table 10 shows an exemplary embodiment of a proposed coupling agent composition according to the invention.

TABLE 10

| Compositional Element | Weight Percent (wt %) | Weight Percent (wt %) |
|---|---|---|
| Deionized water | 75.00-98.00% | 87.55% |
| Mannan | 1.00-3.00% | 1.70% |
| Sodium Phytate | 0.05-0.20% | 0.05% |
| 1,3-Propanediol | 1.00-20.00% | 10.00% |
| Benzyl alcohol (natural sourced) | 0.10-1.50% | 0.50% |
| Xanthan gum | 0.05-1.00% | 0.20% |
| Percent Natural | ~100% | ~100.00% |

In an exemplary description of manufacturing, a coupling agent composition according to the invention is processed according to the following steps. However, one skilled in the art should appreciate that the following steps are merely exemplary and are used to enable one skilled in the art to process proposed coupling agent compositions according to the invention.

In an exemplary embodiment of the invention, a thickening agent, such as a cross-linked polyacrylate, is measured out. A first batch of thickening agent additive, such as a soluble polymer, is measured out and combined with the thickening agent. Next, a first batch of a carrier, such as deionized water, is measured out. The thickening agent and the thickening agent additive are dispersed into the carrier to prepare a first mixture. Next, a first batch of organic natural resource material, such as a polyol, is measured out and combined with a chelating agent and a biocide agent. A mixture of the chelating agent, the first batch of organic natural resource material, and the biocide agent is then added to the first mixture of the carrier and the thickening agent.

Next, a slurry is prepared from a second batch of an organic natural resource material and a second batch of a thickening agent additive. This slurry is added to the mixture of the chelating agent, the first batch of organic natural resource material, the biocide agent, the first mixture of the carrier, and the thickening agent in order to form a source mixture.

Next, a second batch of a carrier is measured out and combined with a neutralizing agent to form a neutralizing mixture. Finally, this neutralizing mixture is combined with the source mixture.

In an embodiment of the invention, the coupling agent is in a clear gel form.

In an embodiment of the invention, the coupling agent has a viscosity greater than or equal to 10,000 centipoise (cP). According to an embodiment of the invention, the coupling agent has a viscosity between 25,000-100,000 cP. According to another embodiment of the invention, the coupling agent has a viscosity between 75,000-90,000 cP. In yet another embodiment of the invention, the coupling agent has a viscosity between 83,200 cP. In yet another embodiment of the invention, the coupling agent has a viscosity between 81,667 cP.

The proposed coupling agent composition according to the invention has excellent acoustics characteristics. Performance specifications (ranges) of the proposed coupling agent composition that would make it useful in medical procedures, including ultrasonic diagnostic procedures, include (1) acoustic velocity, (2) impedance, (3) attenuation, and (4) resolution.

In particular, the proposed coupling agent composition has acoustical velocities very close to that of blood at various temperatures. The limited amount of entrapped air in the tested coupling agents minimized signal attenuation.

Table 11 lists measured acoustic velocities for various known coupling agents and the proposed coupling agent according to the invention tested at 23 C, 32 C and 40 C. Additionally, Table 11 displays the calculated water velocity taken using the Bilaniuk and Wong equation as a marker for test methodology.

TABLE 11

| | Acoustic Velocity (m/s) | | | | | |
|---|---|---|---|---|---|---|
| TEMP C. | Water | PRIOR ART 1 | PRIOR ART 2 | PRIOR ART 3 | Calc water | Proposed Coupling Agent |
| 23 | 1495 | 1561 | 1564 | 1582 | 1491 | 1558 |
| 32 | 1509 | 1572 | 1572 | 1589 | 1513 | Not measured |
| 40 | 1521 | 1579 | 1578 | 1589 | 1528 | 1561 |

FIG. 1 illustrates a comparative chart displaying measured acoustic velocities for various known coupling agents and the proposed coupling agent according to the invention when tested at 23 C, 32 C and 40 C. Additionally, FIG. 1 displays the calculated water velocity taken using the Bilaniuk and Wong equation as a marker for test methodology. As shown, the measured acoustic velocity of the proposed coupling agent is minimally affected by an increase in temperature, as compare to the prior art coupling agents.

In conclusion, the proposed coupling agent provides more consistent acoustic velocity verses prior art couplants. In fact, the test demonstrates more drastic changes in acoustic velocity with increased temperature. When used in imaging, this deviation in acoustic velocity could alter the interpretation of a sonogram, for instance.

The foregoing illustrates some of the possibilities for practicing the invention. Many other embodiments are possible within the scope and spirit of the invention. For instance, the described coupling agent composition could be used for various applications including, but not limited to, ultrasound gels, lubricants, topical gels, and topical treatments. It is, therefore, intended that the foregoing description be regarded as illustrative rather than limiting, and that the scope of the invention is given by the appended claims together with their full range of equivalents.

What is claimed is:

1. A coupling agent composition comprising:
   a plurality of non-toxic components in an amount equal to or greater than 97 weight percent (wt %) of the composition by volume, the plurality of non-toxic components comprising:
   a carrier of water;
   at least one water soluble polyol selected from the group consisting of propanediol, pentylene glycol, and butylene glycol in an amount of from about 1.0 to about 20.0 wt %;
   a thickening agent in an amount of about 0.05 to about 5.00 wt %; and
   a remainder of the composition containing a balance of incidental impurities.

2. The composition according to claim 1, wherein the at least one water soluble polyol is selected from the group consisting of 1,3-propanediol, 1,5-pentylene glycol, and 1,3-butylene glycol.

3. The composition according to claim 1, wherein the thickening agent is a non-toxic swellable polymer.

4. The composition according to claim 3, wherein the thickening agent includes at least one cross-linked polymer selected from a group consisting of hydrophobic polyacrylate or hydrophilic polyacrylate.

5. The composition according to claim 4, wherein the cross-linked polymer is acrylate/C10-30 alkyl acrylate crosspolymer.

6. The composition according to claim 5, wherein the at least one cross-linked polymer is in an amount of from 0.05 to 1.0 weight percent by volume.

7. The composition according to claim 1, wherein the viscosity of the composition is 75,000-90,000 centipoise.

8. The composition according to claim 1, wherein the plurality of non-toxic components further includes a naturally derived soluble polymer additive selected from a group consisting of xanthan gum, guar, locust bean, sodium hyaluronate, carrageenan, sodium alginate, acacia, tara gum, tamarind seed, mannan, succinoglycan, and scleroglucan.

9. The composition according to claim 8, further comprising a biocide agent selected from the group consisting of phenoxyethanol, benzyl alcohol, caprylyl glycol, ethylhexylglycerin, decylene glycol, and 1,2-hexanediol.

10. The composition according to claim 9, further comprising a neutralizing agent selected from a group consisting of sodium hydroxide, triethanolamine, tromethamine, arginine, and lysine.

11. The composition according to claim 10, further comprising a chelating agent selected from a group consisting of disodium EDTA and sodium phytate.

12. The composition according to claim 1, wherein the at least one naturally derived water soluble polyol is processed from a fermentation or enzymatic synthesis.

13. The composition according to claim 12, wherein the fermentation or enzymatic synthesis is a natural chemical process using bacteria or yeast to convert organic materials.

14. The composition according to claim 1, wherein a viscosity of the composition is 25000-100000 centipoise.

15. The composition according to claim 1, wherein the plurality of non-toxic components is propylene glycol free.

* * * * *